United States Patent
Tomov et al.

(10) Patent No.: US 6,818,714 B1
(45) Date of Patent: Nov. 16, 2004

(54) METHOD FOR POLYMERIZING OLEFINS IN THE PRESENCE OF NICKEL COMPLEXES AND CORRESPONDING CATALYTIC SYSTEM

(75) Inventors: Atanas Tomov, Croydon (GB); Roger Spitz, Lyons (FR); Thierry Saudemont, Jurancon (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/936,902

(22) PCT Filed: Mar. 16, 2000

(86) PCT No.: PCT/FR00/00639

§ 371 (c)(1),
(2), (4) Date: Feb. 4, 2002

(87) PCT Pub. No.: WO00/56744

PCT Pub. Date: Sep. 28, 2000

(30) Foreign Application Priority Data

Mar. 19, 1999 (FR) .............................. 99 03463

(51) Int. Cl.$^7$ .................................. C08F 4/44
(52) U.S. Cl. ....................... 526/171; 526/172; 502/152; 502/155
(58) Field of Search ................... 526/171, 172; 502/152, 155

(56) References Cited

U.S. PATENT DOCUMENTS

| | | |
|---|---|---|
| 3,635,937 A | 1/1972 | Bauer et al. |
| 3,637,636 A | 1/1972 | Bauer et al. |
| 3,647,914 A | 3/1972 | Glockner et al. |
| 3,661,803 A | 5/1972 | Bauer et al. |
| 3,686,159 A | 8/1972 | Bauer et al. |
| 4,716,205 A | * 12/1987 | Klabunde .................. 526/115 |

FOREIGN PATENT DOCUMENTS

| | | |
|---|---|---|
| BG | 51624 | 7/1993 |
| BG | 60 319 | 5/1994 |
| WO | WO 97/17380 | 5/1997 |

OTHER PUBLICATIONS

Kurtev et al., Binuclear nickel–ylide complexes as effective ethylene oligomerization/polymerization catalysts, Journal of Molecular Catalysis A: Chemical 103 (1995) pp. 95–103.*

Kurtex, K. et al., "Ethene Polymerization by Binuclear Nickel–ylide Complexes", J. Mol. Catal. (1994), 88(2), 141–50, XP000853888.

Keim, Wilhelm et al., "Reactions of Chelate Ylides With Nickel (0) Complexes", Organometallics (1986), 5(11), 2356–9, XP000856037.

* cited by examiner

*Primary Examiner*—Robert D. Harlan
(74) *Attorney, Agent, or Firm*—Smith, Gambrell & Russell, LLP

(57) ABSTRACT

This system consists of (A) at least one ligand (I) and (B) at least one nickel compound chosen from nickel complexes of zero oxidation state; π-allylnickels; and compounds of the bis(allyl)nickel type

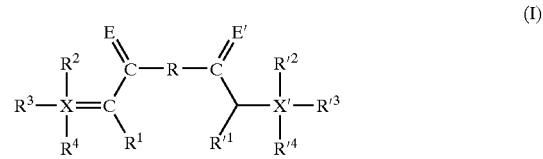

(I)

where E, E'=O, S; X, X'=P, As, Sb; $R^1$, $R'^1$=H, alkyl, aryl, arylalkyl, alkylaryl, halogen, OH, alkoxide

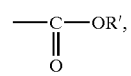

where R'=a hydrocarbon radical of the $C_1$–$C_{15}$ type;
—$SO_3Y$ where Y=Li, Na, $NH_4^+$, $NR''_4^+$ (R''=$C_1$–$C_{15}$ hydrocarbon radical); $R^2$, $R'^2$, $R^3$, $R'^3$, $R^4$ and $R'^4$= alkyl, arylalkyl; and R=divalent radical.

46 Claims, No Drawings

METHOD FOR POLYMERIZING OLEFINS IN THE PRESENCE OF NICKEL COMPLEXES AND CORRESPONDING CATALYTIC SYSTEM

FIELD OF THE INVENTION

The present invention relates to the polymerization of olefins in the presence of a bimetallic complex of nickel formed in situ.

The polymers of ethylene and other olefins are of considerable commercial attraction. The applications of these polymers are extremely numerous, from low molecular weight products for lubricants and greases, to higher molecular weight products for manufacturing fibers, films, molded articles, elastomers, etc. In the majority of cases, the polymers are obtained by catalytic polymerization of olefins by means of a transition-metal-based compound. The nature of this compound has a very strong effect on the properties of the polymer, its cost and its purity. Given the importance of polyolefins, there is a continuous need to improve the catalytic systems and to provide new ones thereof.

BACKGROUND OF THE INVENTION

There is a variety of homogeneous or heterogeneous catalysts for polymerizing or copolymerizing ethylene. Among the best-known families, mention may be made, for example, of the catalysts of the "Ziegler" type involving organometallic complexes of group III and IV metals or catalysts of the "Phillips" type involving chromium complexes. However, there are also nickel-based catalysts used in particular for a number of years for producing α-olefins. In addition, some systems have a degree of tolerance toward polar media.

Among the numerous catalytic systems mentioned in the literature, the association between a nickel complex, such as bis(1,5-cyclooctadiene), with benzoic acid derivatives such as 2-mercaptobenzoic acid or 3,5-diaminobenzoic acid (U.S. Pat. No. 3,637,636) or with chelating tertiary organophosphorus ligands (U.S. Pat. No. 3,635,937, U.S. Pat. No. 3,647,914) or even with glycolic, thioglycolic or thiolactic acids (U.S. Pat. No. 3,661,803) has, for example, been described. The use of a nickel complex in its zero oxidation state, such as again bis(1,5-cyclooctadiene), with a phosphorus ylid ligand, is described in U.S. Pat. No. 3,686,159. The inventions above have in common the in situ formation of the active species in the polymerization medium.

Other methods, such as in U.S. Pat. No. 4,716,205 or Bulgarian patent BG 60319 or in J. Mol. Catal. (1994), 88(2), 141–50 or in J. Mol. Catal. (1995), 103, 95–103, claim catalytic nickel systems which can be isolated, but it is necessary to introduce an accepter compound capable of extracting one of the ligands from the nickel complex in order to make it active, into the polymerization medium. The in situ technique does not allow isolation of the catalytic system so as to identify its structure accurately, but the approach has the merit of being simple and it limits the handling of catalysts, which is a so of pollution.

DESCRIPTION OF THE INVENTION

The present invention relates to the use of new ligands which, used in situ with a nickel complex in the zero oxidation state in the presence of at least one olefin, such as ethylene or a mixture of ethylene with one or more other olefins, make it possible to obtain a polyolefin such as polyethylene or a high-mass ethylene copolymer, with very high activity even in the presence of a polar medium.

The subject of the present invention is therefore firstly a catalytic system characterized in that it consists of:

(A) at least one ligand which can be represented by the general formula (I):

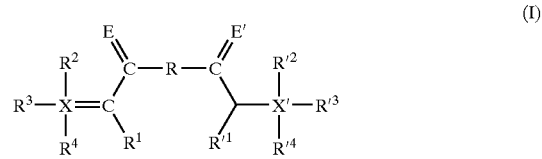

where:

E and E' each represent independently an oxygen or a sulfur atom;

X and X' each represent independently a phosphorus, arsenic or antimony atom;

the radicals $R^1$ and $R'^1$, which may be identical or different, are chosen from:
hydrogen;
linear, branched or cyclic alkyl radicals;
aryl radicals;
arylalkyl radicals;
alkylaryl radicals;
halogens;
the hydroxyl radical;
alkoxide radicals;

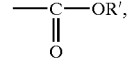

where R' represents a hydrocarbon radical which may have from 1 to 15 carbon atoms;
—$SO_3Y$, where Y is chosen from Li, Na, $NH_4^+$, $NR''^+_4$ (where R" represents a hydrocarbon radical which may have from 1 to 15 carbon atoms);

the $R^2$, $R'^2$, $R^3$, $R'^3$, $R^4$ and $R'^4$ radicals, which may be identical or different, are chosen from linear branched or cyclic alkyl radicals, and arylalkyl radicals; and R is a divalent radical; and (B) at least one nickel compound chosen from:

(B1) nickel complexes of zero oxidation state, which can be represented by the general formula (II):

where $R^a$ and $R^b$ each represent independently a hydrogen atom, or a linear, branched or cyclic alkyl radical or aryl, arylalkyl or alkylaryl radical, which may have up to 8 carbon atoms, it being possible for $R^a$ and $R^b$ to form together a divalent aliphatic group of 2 to 10 carbon atoms and be able to have up to three olefinic double bonds as the only carbon-carbon unsaturated groups;

(B2) π-allylnickels, which can be represented by the general formula (III):

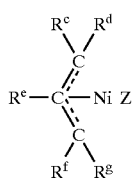

in which:

the $R^c$, $R^d$, $R^e$, $R^f$ and $R^g$ radicals, which may be identical or different, are chosen from hydrogen, linear, branched or cyclic alkyl radicals and aryl, arylalkyl or alkylaryl radicals, having up to 8 carbon atoms;

the dotted lines represent the electron delocalization on the three contiguous carbon atoms;

an $R^c$ or $R^d$ radical may form, with an $R^e$ or $R^f$ or $R^g$ radical, a divalent alkene group having from 2 to 10 carbon atoms and able to have up to three olefinic double bonds; and Z represents a halogen, preferably a chlorine or bromine atom, an alkoxy group or an alkanoyloxy group, these groups possibly having in particular from 1 to 10 carbon atoms;

(B3) compounds of the bis(allyl)nickel type which can be represented by the general formula (IV):

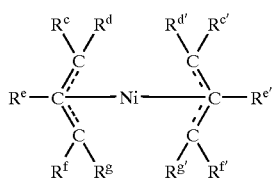

in which:

the radicals $R^e$ to $R^g$, and $R^{e'}$ to $R^{g'}$, which may be identical or different, are chosen from hydrogen, linear, branched or cyclic alkyl radicals and aryl, arylalkyl or alkylaryl radicals having up to 8 carbon atoms;

the dotted lines represent the electron delocalization on the three contiguous carbon atoms;

a radical $R^c$ or $R^d$ able to form, with a radical $R^e$ or $R^f$ or $R^g$, a divalent alkene group having from 2 to 10 carbon atoms, preferably from 2 to 5 carbon atoms, and able to have up to three olefinic double bonds;

a radical $R^{c'}$ or $R^{d'}$ able to form, with a radical $R^{e'}$ or $R^{f'}$ or $R^{g'}$, a divalent alkene group having from 2 to 10 carbon atoms, preferably from 2 to 5 carbon atoms, and able to have up to three olefinic double bonds.

In formula (I), E and E' are preferably separated by intermediate atoms linked together by covalent or coordinate bonds; again preferably, the minimum number of atoms between E and E' in formula (I) is from 3 to 40. The term minimum number of atoms between E and E' refers to the minimum number of atoms encountered in the molecule on going from atom E to atom E' along the bonds atom by atom. By way of example, if the ligand comprises the structure:

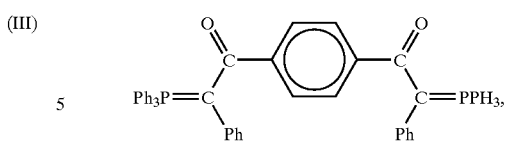

where Ph represents a phenyl radical, the minimum number of atoms between the oxygen atoms is 6, since it is not possible to encounter fewer than 6 atoms on going from the first oxygen to the second oxygen.

Moreover, in formula. (I), R is chosen in particular from:

divalent hydrocarbon radicals comprising, for example, from 2 to 38 carbon atoms, such as alkylene, alkenylene, arylene, cycloalkylene, bicycloalkylene and alkylarylene radicals; and the 1,1'-ferrocenylene radical which is possibly substituted, for example, with one or two monovalent radicals such as

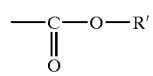

or —$SO_3Y$, R' and where Y has the meanings already given.

By way of examples, the ligand of formula (I) may be one of those comprising the following structures:

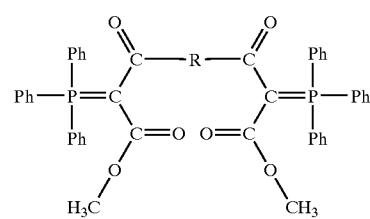

where R represents a 5,6-bicyclo[2.2.1]-hept-2-ene radical; —$(CH_2)_4$— or —$(CH_2)_8$—;

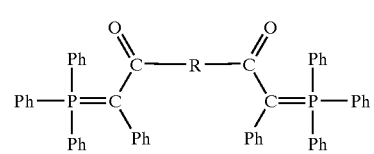

where R represents a 5,6-bicyclo[2.2.1]-hept-2-ene radical; or —$(CH_2)_8$—;

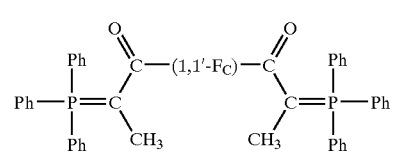

where 1,1'-F$_c$ represents a -1,1'-ferrocenylene radical; and

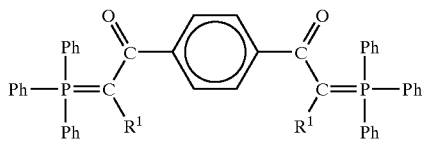
(Id)

where R$^1$ presents H or Ph or SO$_3$Na or

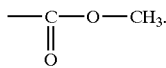

The 5,6-bicyclo[2.2.1]hept-2-ene radical can be represented by:

By way of examples of nickel compounds (B$_1$), of the first family mentioned of olefinic nickel compounds which can be used as catalytic precursors, mention may be made of:

bis(1,5-cyclooctadiene)nickel(0);
bis(cyclooctatetraene)nickel(0); and
bis(1,3,7-octatriene)nickel(0).

The π-allyl nickels (B2) are another family of olefinic nickel compounds which can be used as catalytic precursors. In these compounds, the nickel entity is linked to a π-allyl group characterized by delocalization of the electron contribution from the π-allyl group over three contiguous carbon atoms.

In the nickel compounds (B2) and in the compounds of the nickel bis-allyl type (B3)—forming the third family of olefinic nickel compounds which can be used as catalytic precursors—a π-allyl group has from 3 to 12 carbon atoms which do not have other aliphatic unsaturated groups, except if it contains a closed ring.

By way of examples of nickel compounds (B2), mention may be made of:

π-allylnickel chloride;
π-allylnickel bromide;
π-crotylnickel chloride;
π-methylallylnickel chloride;
π-ethylallylnickel chloride;
π-cyclopentylallylnickel bromide;
π-cyclooctenylnickel chloride;
π-cyclooctadienylnickel chloride;
π-cynnamylnickel bromide;
π-phenylallylnickel chloride;
π-cyclohexenylnickel bromide;
π-cyclododecenylnickel chloride;
π-cyclododecatrienylnickel chloride;
π-allylnickel acetate;
π-methylallylnickel propionate;
π-cyclooctenylnickel octoate;
π-cyclooctenylnickel methoxylate; and
π-allylnickel ethoxylate.

Although the halides (B2) above probably exist independently in the form of dimers, for clarity of the present description they are mentioned in the form of monomeric species.

By way of example of nickel compounds (B3) mention may be made of:

bis(π-allyl)nickel;
bis(π-methallyl)nickel;
bis(π-cynnamyl)nickel;
bis(π-octadienyl)nickel;
bis(π-cyclohexenyl)nickel;
π-allyl-π-ethallylnickel; and
bis(π-cyclooctatrienyl)nickel.

Preferably, the components (A) and (B) are present in amounts such that the nickel-to-ligand(s) molar ratio is between 1 and 100, more preferably between 2 and 50.

The subject of the present invention is also a process for the polymerization of at least one olefin in the presence of a catalytic system as defined above, in a diluting medium.

According to one particularly preferred embodiment of the process according to the invention, in a first step, each of the constituents (A) and (B), which are in solution in an inert solvent, are introduced separately or simultaneously into a reactor, together with the reaction mixture; and in a second step, the olefin or olefins are introduced, the (co)polymerization taking place at a temperature between 0 and 300° C., preferably between 25 and 250° C., and at a total absolute pressure of from 1 to 200 bar, preferably from 1 to 100 bar.

As indicated above, the constituents (A) and (B) are introduced in a nickel-to-ligand(s) molar ratio of between 1 and 100, and more preferably between 2 and 50.

The inert solvent in which the constituents (A) and (B) are found for the first step is a solvent compatible with the operations to be carried out. By way of examples of such solvents, mention may be made of all those compatible with the polymerization of olefins by organometallic catalysis, in particular saturated aliphatic, saturated alicyclic and aromatic hydrocarbons such as isobutane, butane, pentane, hexane, heptane, isododecane, cyclohexane, cycloheptane, methylcyclohexane, methylcycloheptane, toluene, ortho-xylene, para-xylene and any mixture of the above compounds.

The inert solvents of each of the constituents (A) and (B) may be identical or different.

The reaction mixture of the process according to the invention may consist of an organic medium, or else it may comprise a continuous liquid aqueous phase, which comprises more than 30% water by weight. In the latter case, the aqueous phase may be the only liquid phase of the reaction mixture (except for the solutions of the constituents (A) and (B)). Also in this case, the mixture may comprise a liquid organic phase.

The concentration of the constituent (A) in the inert solvent is preferably between 0.1 micromol and 100 millimol per liter of solution; and the concentration of the constituent (B) in the inert solvent is preferably between 0.1 micromol and 200 millimol per liter of solution.

The process according to the invention is generally carried out in an inert atmosphere.

In a preliminary step, the constituents (A) arid (B) can be brought into contact with each other in solution in their inert solvent, for a duration of 30 seconds to 15 minutes, preferably of 30 seconds to 10 minutes, before their introduction into the reaction mixture, this precontacting step also being carried out in an inert atmosphere, at a temperature of between 0 and 100° C., in particular between 10 and 70° C.

The constituents (A) and (B), which are found in solution in their inert solvent, may also be introduced separately in no preferred order into the reaction mixture, the latter being held at a temperature of from 0 to 100° C., in particular from 10 to 70° C.

It is possible to choose the polymerization medium (organic medium) or the organic phase of a polymerization medium comprising a liquid aqueous phase from:

saturated aliphatic hydrocarbons, saturated alicyclic hydrocarbons, aromatic hydrocarbons and mixtures thereof, in particular from isobutane, butane, pentane, hexane, heptane, isododecane, cyclohexane, cycloheptane, methylcyclohexane, methylcycloheptane, toluene, ortho-xylene, para-xylene and any mixture of these compounds; and to the extent that the polymerization conditions keep them in liquid form, α-olefins, such as propylene, butene, hexene or 4-methyl-1-pentene, unconjugated dienes, such as 1,9-decadiene, 1,5-hexadiene, 1,13-tetradecadiene, biscyclo[2.2.1]-hepta-2,5-diene, and mixtures thereof.

This organic medium could also be chosen from alcohols, being, for example, a monoalcohol or a diol, comprising, for example, 5 to 20 carbon atoms; ethers comprising, for example, 3 to 15 carbon atoms, such as, for example, tetrahydrofuran or dioxane; and esters comprising, for example, from 2 to 15 carbon atoms, such as, for example, ethyl, butyl or vinyl acetate, ormethyl acrylate.

Where the polymerization medium comprises an aqueous phase, during the polymerization, the polymerization medium comprises said liquid aqueous phase, a solid phase consisting of the solid polymer arising from the polymerization, and it also comprises, depending on the physical state of the olefin to be polymerized, at least one other gaseous phase and/or one other liquid phase. If an olefin to be polymerized is liquid under the conditions of temperature and pressure of the polymerization, this olefin will be able to be part of a liquid organic phase distinct from the liquid aqueous phase. Such a liquid organic phase may also comprise an organic solvent, such as those indicated above, of said olefin.

The constituents of any liquid organic phase are sufficiently insoluble in water such that, given the quantity thereof involved, the aqueous phase always contains more than 30% water.

Where the polymerization medium comprises two distinct liquid phases, the latter may, for example, be present such that the phase other than the aqueous phase represents 1 to 50% by volume of the aqueous phase.

The aqueous phase may comprise at least 40%, or even at least 50%, or even at least 60%, or even at least 70%, or even at least 80% by weight of water.

The aqueous phase may comprise, in dissolved form, an organic compound which could be an alcohol or a ketone or a diol such as a glycol, for example ethylene glycol, or propanediol or butanediol. This organic compound may have the function of increasing the solubility in the aqueous phase of the olefin to be polymerized.

The polymerization medium is preferably stirred. The stirring is preferably enough to distribute the various phases uniformly in the reactor.

At least one dispersing agent can be added to the polymerization medium. Such a dispersing agent may in particular be used when the polymerization medium comprises a liquid organic phase, in which case it helps to disperse said liquid organic phase in the form of droplets surrounded by the continuous aqueous phase. In this case, since the constituents (A) and (B) have been mainly dissolved in the liquid organic phase, the polymerization takes place mainly in the droplets, the latter generally having a mean diameter of between 10.0 μm and 3 millimeters.

The dispersing agent may be one of those known to have this function, such as, for example, a polyvinyl alcohol, methylcellulose, a gelatine, kaolin, barium sulfate, hydroxyapatite, magnesium silicate, tricalcium phosphate, or a combination of several of these dispersing agents.

The dispersing agent may be introduced into the polymerization medium at up to 10% by weight with respect to the water used and preferably from 0.01% to 5% by weight with respect to the weight of water used.

At least one emulsifying agent can be added to the polymerization medium. The use of such an emulsifying agent is in particular recommended when it is desired that the polymerization leads to a latex, that is to say to an ensemble of polymer particles having a number-average diameter of less than 1 micrometer, said particles being dispersed in the aqueous phase. When an emulsifying agent is used, it is not generally necessary for the polymerization medium to contain a dispersing agent.

By way of example of an emulsifying agent, it is possible to use any one of the known surfactants, whether they be anionic, nonionic or even cationic. In particular, it is possible to choose the emulsifying agent from anionic agents such as the sodium or potassium salts of fatty acids, in particular sodium laurate, sodium stearate, sodium palmitate, sodium oleate, the mixed sulfates of sodium or potassium and of a fatty alcohol, especially sodium laurylsulfate, the sodium or potassium salts of sulfosuccinic esters, the sodium or potassium salts of alkylarylsulfonic acids, in particular sodium dodecylbenzenesulfonate, and the sodium or potassium salts of monosulfonates of fatty monoglycerides, or even from nonionic surfactants such as the products of the reaction between ethylene oxide and alkylphenols. It is of course possible to use mixtures of such surfactants.

The emulsifying agent can be introduced into the polymerization medium at up to 10% by weight with respect to the weight of water, and preferably from 0.01% to 5% by weight with respect to the weight of water.

In such a process comprising an emulsifying agent and a liquid organic phase, since the constituents (A) and (B) have mainly been dissolved in said liquid organic phase, and since the amount of emulsifying agent is greater than the critical micelle concentration, the polymerization takes place in the liquid organic phase droplets, which generally have a mean diameter of between 1 μm and 1 000 μm, and in the micelles which generally have a mean diameter of between 1 nanometer and 100 nanometers. Such a process is similar to the process called "radical emulsion polymerization", except that it does not involve radicals. When, in such a process, the concentration of emulsifying agent is increased, the relative extent of the polymerization taking place in the micelles is increased, promoting the formation of a latex at the end of polymerization. When in this case a liquid organic phase is present and when the amount of emulsifying agent is such that all the liquid organic phase is present in the micelles, the process is similar to the process called "radical microemulsion polymerization", except that the polymerization does not involve radicals.

Where the polymerization medium comprises a liquid organic base and an emulsifying agent, it is possible to add a cosurfactant to the medium, as happens for the polymerization processes in a miniemulsion. Such a cosurfactant generally has a solubility in water of less than $1\times10^{-3}$ mol per liter at 20° C. Such a cosurfactant may, for example, be hexadecane or cetyl alcohol. It may be present at up to 10% by weight with respect to the weight of water and preferably the ratio of the mass of emulsifying agent to that of the cosurfactant ranges from 0.5 to 2. The presence of this cosurfactant makes it possible, also by means of enough shearing of the medium, to obtain droplets of the liquid organic phase of less than 1 μm and promotes the formation of a latex at the end of polymerization. Enough shearing may, for example, be obtained by ultrasound or by a homogenizer (such as an apparatus of the Ultraturax or Diax 600 type from Heidolph). Once the characteristic size (<1 μm) of the droplets is obtained, stirring can be continued with less vigorous shearing, of the type of shearing used for suspension polymerization processes.

Where an organic solvent has been used, the latter can, if desired, be removed by evaporation.

The process according to the invention leads to polymer particles whose diameter may range from 10 nanometers to 5 millimeters.

Where the polymerization comprises an emulsifying agent, a latex is obtained. At the end of the polymerization carried out in the presence of an emulsifying agent, the latex possibly contains particles having a tendency to separate by settling and it may be desirable to carry out a separation, for example by filtration, so as to remove those particles not forming part of the latex.

The polymerization conditions, namely the amount of ingredients in the polymerization medium and the degree of conversion of monomer into a polymer, may be adapted so that the latex has a solids content ranging from 0.1 to 50% by weight.

The olefin intended to be polymerized is introduced with enough stirring of the polymerization medium, for example stirring ranging from 10 to 10 000 revolutions per minute. The olefin may be introduced in liquid or gaseous form, depending on its physical state.

The polymerization temperatures and pressures have been indicated above.

Where only ethylene is polymerized, a high-density polyethylene homopolymer is obtained. The polymerization of ethylene with at least one olefin other than ethylene leads to the production of a lower-density ethylene polymer than the abovementioned high-density polyethylene homopolymer. Depending on the amount and the type of the comonomer(s) of ethylene, it is therefore possible to obtain a high-density ethylene polymer (high-density polyethylene), or a medium-density ethylene polymer (medium-density polyethylene) or even, with a high proportion of comonomer, a low-density ethylene polymer (low-density polyethylene).

As is common practice for ethylene polymers, the term "high density" means a density greater than 0.940, medium density means that the density ranges from 0.925 to 0.940 and low density means that the density is less than 0.925.

The polymerization may therefore lead to a latex of at least one olefin, that is to say to a polymer comprising polymerized units of at least one olefin, with other units of polymerized monomer if necessary. In particular, if at least one olefin is ethylene, a latex of an ethylene polymer can be obtained.

The process according to the invention may therefore, lead to a latex of a high-density ethylene polymer or to a latex of a medium-density ethylene polymer, or even of a low-density ethylene polymer.

Within the scope of the present patent application, the term polymer must be taken in its general sense, such that it covers homopolymers, copolymers, interpolymers and polymer blends. The term polymerization must also be taken in an equivalent general sense.

The set of olefins includes that of the α-olefins. As olefins, mention may be made of ethylene, propylene, cyclopentene, 1-hexene, 3-methyl-1-pentene, 4-methyl-1-pentene, 1,4-hexadiene, 1,9-decadiene, 1-octene, 1-decene, and the cyclic olefins such as cyclohexene. The set of olefins also includes the compounds of formula $CH_2=CH-(CH_2)_n-G$ where n is an integer ranging from 2 to 20, and G represents a radical which can be chosen from the following list:

—OH, —CHOHCH$_2$OH, —OT, —CF$_3$, —COOT, —COOH, —Si(OH)$_3$, —Si(OT)$_3$, where T is a hydrocarbon radical having from 1 to 20 carbon atoms. Mention is made in particular of the cases where at least one olefin is ethylene.

The process according to the invention may be carried out in batches, semicontinuously or continuously.

EXAMPLES

The following examples illustrate the present invention without however limiting the scope thereof. In these examples, the following abbreviations have been used:

weight-average molecular mass: $\overline{M}_w$ polydispersity (weight-average molecular mass/number-average mass): $\overline{M}_w/\overline{M}_n$.

Example 1

Polymerization of Ethylene 42 ml of toluene and 67 mg of exo,endo-2,3-bis[2-methoxycarbonyl-2-(triphenylphosphoranylidene)acetyl] bicyclo[2.2.1]hept-5-ene ligand, that is a concentration of 1.9 μmol/ml were placed in a 200 ml Schlenck tube in a nitrogen atmosphere (Solution 1).

41.2 ml of toluene and 56 mg of bis(1,5-cyclooctadienyl) nickel, that is a concentration of 4.9 μmol/ml, were placed in a second 200 ml Schlenck tube (Solution 2).

500 ml of toluene, 10 ml of Solution 2 and 5 ml of Solution 1, that is a nickel/ligand molar ratio of 5, were introduced at ambient temperature successively into a 1 liter metal reactor, fitted with a stirrer, in a nitrogen atmosphere and with stirring at 250 rpm. The reaction mixture was then kept at 1 bar nitrogen and at 65° C. for 10 minutes.

Ethylene was then introduced so that there was an absolute pressure in the reactor of 5 bar. The pressure was kept constant throughout the polymerization by means of a continuous feed of ethylene into the reactor.

After one hour of polymerization, 86 g of polyethylene, that is a productivity of $8.8\times10^6$ g of polymer/mole of ligand, were recovered.

The polyethylene had the following characteristics:

$\overline{M}_w$=35.600 g/mol;

$\overline{M}_w/\overline{M}_n$=10.2;

Melting point (measured by DSC—Differential Scanning Calorimetry)=129.4° C.

Example 2

Polymerization of Propylene 51 ml of toluene and 86 mg of exo,endo-2,3-bis-[2-methoxycarbonyl-2-(triphenylphosphoranylidene)acetyl] bicyclo[2.2.1]hept-5-ene ligand, that is a concentration of 2.6 μmol/ml, were placed in a 200 ml Schlenck tube, in a nitrogen atmosphere (Solution 3).

37.1 ml of toluene and 101 mg of bis(1,5-cyclooctadienyl) nickel, that is a concentration of 2.6 μmol/ml, were placed in a second 200 ml Schlenck tube (Solution 4).

500 ml of toluene, 10 ml of Solution 4 and 5 ml of Solution 3, that is a nickel/ligand molar ratio of 9.6, were introduced at ambient temperature successively into a 1 liter metal reactor, fitted with a stirrer in a nitrogen atmosphere and with stirring at 250 rpm. The reaction mixture was then kept at 1 bar nitrogen and at 65° C. for 10 minutes.

Polypropylene was then introduced so that there was an absolute pressure in the reactor of 5 bar. The pressure was kept constant throughout the polymerization by means of a continuous feed of polypropylene into the reactor.

After one hour of polymerization, a yellowish solution was recovered which, after evaporation, provide 1 g of a polymer having the appearance of a grease. The productivity was $0.1 \times 10^6$ g of polymer/mol of ligand.

$\overline{M}_w$=6 941 g/mol;

$\overline{M}_w/\overline{M}_n$=4.5;

The melting point (measured by DSC) was 119° C.

Example 3

Copolymerization of Ethylene and Propylene 56.8 ml of toluene and 91 mg of exo,endo-2,3-bis-[2-methoxycarbonyl-2-(triphenylphosphoranylidene)acetyl] bicyclo[2.2.1]hept-5-ene ligand, that is a concentration of 2.0 μmol/ml, were placed in a 200 ml Schlenck tube, in a nitrogen atmosphere (Solution 5).

91.4 ml of toluene and 132 mg of bis(1,5-cyclooctadiehyl) nickel, that is a concentration of 5.3 μmol/ml, were placed in a second 200 ml Schlenck tube (Solution 6).

500 ml of toluene, 20 ml of Solution 6, and 5 ml of Solution 5, that is a nickel/ligand molar ratio of 10.8, were introduced at ambient temperature successively into a 1 liter metal reactor, fitted with a stirrer in a nitrogen atmosphere and with stirring at 250 rpm. The reaction mixture was then kept at 1 bar nitrogen and at 65° C. for 10 minutes.

A gas mixture of 80/20 ethylene/propylene by mass was then introduced so that the absolute pressure in the reactor was 5 bar. The pressure was kept constant throughout the polymerization by means of a continuous feed of the 80/20 by mass ethylene/propylene mixture into the reactor.

After one hour of polymerization, 92 g of a polymer having the appearance of a grease was recovered. The productivity was $9.4 \times 10^6$ g of polymer/mol of ligand.

$\overline{M}_w$=4 166 g/mol $\overline{M}_w/\overline{M}_n$=2.9.

Infrared analysis of the product indicates an incorporation of propylene not exceeding 5%.

Example 4

Emulsion Copolymerization of Ethylene and Propylene 1.5 l of deionized water, through which nitrogen had bubbled for 24 h, was introduced into a 2.5 l Schlenck tube. 200 ml of this water were taken and introduced into a 300 ml Schlenck tube with 6 g of sodium laurylsulfate (SLS) and sparged with nitrogen for 2 hours. 3 ml of hexadecane were then added. The contents of the second Schlenck tube were reintroduced into the first tube.

35 mg of the exo, endo-2,3-bis[2-methoxycarbonyl-2 (triphenylphosphoranylidene)acetyl]bicyclo[2.2.1]hept-5-ene ligand and 263 mg of bis(cis,cis-1,5-cyclooctadiene) nickel in powder form (that is a nickel/ligand molar ratio of 22.2) were introduced into a 200 ml Schlenck tube followed by 50 ml of toluene; the mixture was then stirred for 1 minute at ambient temperature. This solution was added to the aqueous phase. The whole was then homogenized, still in a nitrogen atmosphere, by means of an Ultraturax homogenizer for 1 minute at 1 500 revolutions per minute. The miniemulsion obtained was introduced into a 6 l metal reactor fitted with a mechanical stirrer and kept at 45° C.

The reactor was placed at 2 bar of a 76/24 by mass ethylene/propylene mixture, and its temperature was raised to 65° C. with stirring at 400 revolutions per minute. When the temperature had reached 65° C., the ethylene pressure was raised to 20 bar and kept constant for 1 hour.

The temperature was then reduced to 20° C. and the reactor was progressively degassed over 20 minutes. 29.3 g of polymer, in the form of a dispersion which sediments slowly, was recovered. The melting point of the recovered product was 110° C.

What is claimed is:

1. A catalytic system for the polymerization of at least one olefin in a diluting medium in the presence of the catalytic system, the catalytic system being formed in situ from:

(A) at least one ligand selected from the group consisting of:

a ligand represented by formula (Ia):

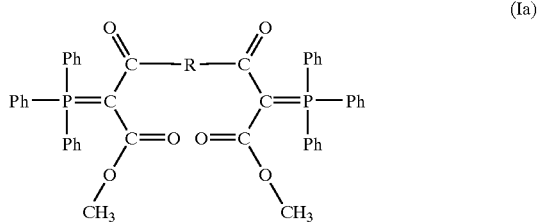

(Ia)

where R represents a 5,6-bicyclo[2.2.1]hept-2-ene radical; —(CH$_2$)$_4$;— or —(CH$_2$)$_8$—;

a ligand represented by formula (Ib):

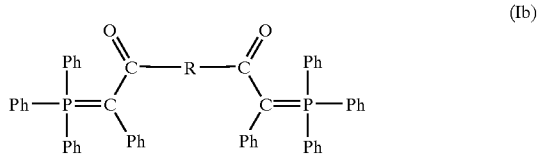

(Ib)

wherein R represents a 5,6bicyclo[2.2.2]-hept-2-ene radical or —(CH$_2$)$_8$—;

a ligand represented by formula (Ic):

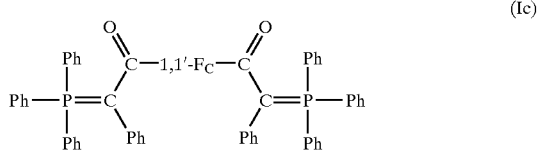

(Ic)

where 1,1'-F$_c$ represents a-1,1'-ferrocenylene radical;

a ligand represented by formula (Id'):

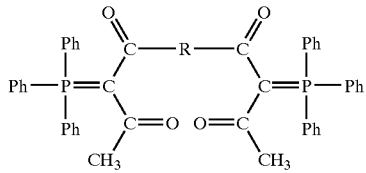
(Id')

where R represents a pheny radical of the formula 1,4-C$_6$H$_4$; and a ligand represented by formula (I)':

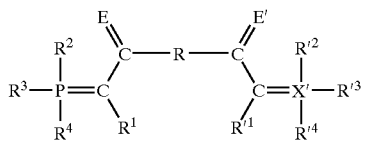
(I)' where:
E and E' each represent independently an oxygen or a sulfur atom;
X and X' each represent independently a phosphorus, arsenic or antimony atom;
the radicals R$^1$ and R$^{'1}$, which are identical or different, are selected from the group consisting of:
  branched or cyclic alkyl radicals;
  arylalkyl radicals;
  alkylaryl radicals;
  halogens;
  hydroxyl radical; and
  alkoxide radicals;
the R$^2$, R$^{'2}$, R$^3$, R$^{'3}$, R$^4$ and R$^{'4}$ radicals, which are identical or different, are selected from the group consisting of linear, branched or cyclic alkyl radicals; and
R is a divalent radical; and (B) at least one nickel compound selected from:
(B1) nickel complexes with a zero oxidation state, which are represented by the general formula (II):

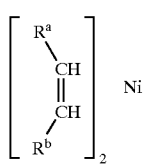
(II)

where R$^a$ and R$^b$ each represent independently a hydrogen atom, or a linear, branched or cyclic alkyl radical or aryl, arylalkyl or alkylaryl radical, which have up to 8 carbon atoms, it being also possible for R$^a$ and R$^b$ to form together a divalent aliphatic group of 2 to 10 carbon atoms and have up to three olefinic double bonds as the only carbon-carbon unsaturated groups;
(B2) π-allylnickels, which are represented by the formula (III):

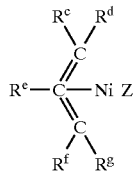
(III)

in which:
the R$^c$, R$^d$, R$^e$, R$^f$ and R$^g$ radicals, which are identical or different, are selected from hydrogen, linear, branched or cyclic alkyl radicals and aryl, arylalkyl or alkylaryl radicals, having up to 8 carbon atoms;
the dotted lines represent the electron delocalization on the three contiguous carbon atoms;
an R$^c$ or R$^d$ radical may also form, with an R$^e$ or R$^f$ or R$^g$ radical, a divalent alkene group having from 2 to 10 carbon atoms and able to have up to three olefinic double bonds; and
Z represents a halogen, an alkoxy group or an alkanoyloxy group;
(B3) compounds of the bis(allyl)nickel type which are represented by the (IV):

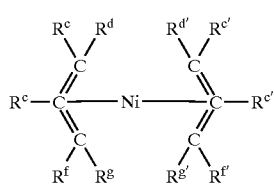
(IV)

in which:
the radicals R$^c$ to R$^g$, and R$^{c'}$ to R$^{g'}$, which are identical or different, are selected from hydrogen, linear, branched or cyclic alkyl radicals and aryl, arylalkyl or alkylaryl radicals having up to 8 carbon atoms;
the dotted lines represent the electron delocalization on the three contiguous carbon atoms;
a radical R$^c$ or R$^d$ also able to form, with a radical R$^e$ or R$^f$ or R$^g$, a divalent alkene group having from 2 to 10 carbon atoms and able to have up to three olefinic double bonds;
a radical R$^{c'}$ or R$^{d'}$ also able to form, with a radical R$^{e'}$ or R$^{f'}$ or R$^{g'}$, a divalent alkene group having from 2 to 10 carbon atoms and able to have up to three olefinic double bonds.

2. The catalytic system of claim 1, wherein the at least one ligand (A) is a ligand represented by formula (Ia'):

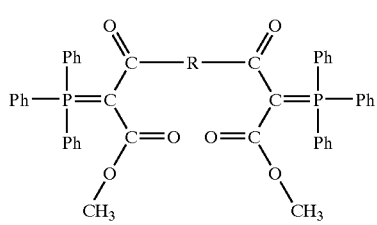
(Ia')

where R represents a 5,6-bicyclo[2.2.1]hept-2-ene radical.

3. A process for the polymerization of at least one olefin in a diluting medium in the presence of a catalytic system, the catalytic system being formed in situ from:

(A) at least one ligand selected from the group consisting of:

a ligand represented by formula (Ia):

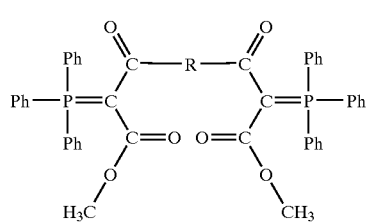
(Ia)

where R represents a 5,6-bicyclo[2.2.1]hept-2-ene radical; —(CH$_2$)$_4$;— or —(CH$_2$)$_8$—;

a ligand represented by formula (Ib):

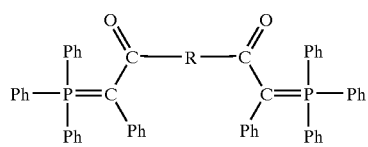
(Ib)

a ligand represented by formula (Ic):

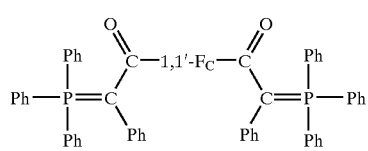
(Ic)

where 1,1'-F$_c$ represents a-1,1'-ferrocenylene radical; and a ligand represented by formula (Id'):

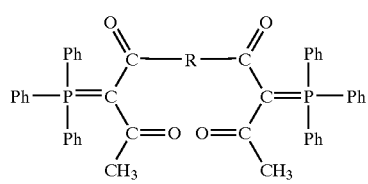
(Id')

where R represents a pheny radical of the formula 1,4-C$_6$H$_4$; and a ligand represented by formula (I)':

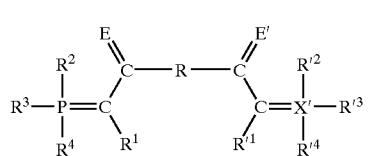
(I)' where:
E and E' each represent independently an oxygen or a sulfur atom;
X and X' each represent independently a phosphorus, arsenic or antimony atom;
the radicals R' and R$^1$, which are identical or different, are selected from the group consisting of:
  branched or cyclic alkyl radicals;
  arylalkyl radicals;
  alkylaryl radicals;
  halogens;
  hydroxyl radical; and
  alkoxide radicals;
the R$^2$, R'$^2$, R$^3$, R'$^3$, R$^4$ and R'$^4$ radicals, which are identical or different, are selected from the group consisting of linear, branched or cyclic alkyl radicals; and
R is a divalent radical; and (B) at least one nickel compound selected from:

(B1) nickel complexes with a zero oxidation state, which are represented by the general formula (II):

(II)

where R$^a$ and R$^b$ each represent independently a hydrogen atom, or a linear, branched or cyclic alkyl radical or aryl, arylalkyl or alkylaryl radical, which have up to 8 carbon atoms, it being also possible for R$^a$ and R$^b$ to form together a divalent aliphatic group of 2 to 10 carbon atoms and have up to three olefinic double bonds as the only carbon-carbon unsaturated groups;

(B2) π-allylnickels, which are represented by the formula (III):

(III)

in which:
the R$^c$, R$^d$, R$^e$, R$^f$ and R$^g$ radicals, which are identical or different, are selected from hydrogen, linear, branched or cyclic alkyl radicals and aryl, arylalkyl or alkylaryl radicals, having up to 8 carbon atoms;
the dotted lines represent the electron delocalization on the three contiguous carbon atoms;
an R$^c$ or R$^d$ radical may also form, with an R$^e$ or R$^f$ or R$^g$ radical, a divalent alkene group having from 2 to 10 carbon atoms and able to have up to three olefinic double bonds; and
Z represents a halogen, an alkoxy group or an alkanoyloxy group;

(B3) compounds of the bis(allyl)nickel type which are represented by the (IV):

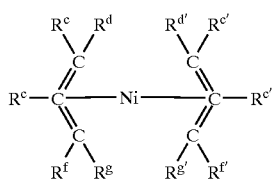

in which:
the radicals $R^c$ to $R^g$, and $R^{c'}$ to $R^{g'}$, which are identical or different, are selected from hydrogen, linear, branched or cyclic alkyl radicals and aryl, arylalkyl or alkylaryl radicals having up to 8 carbon atoms;
the dotted lines represent the electron delocalization on the three contiguous carbon atoms;
a radical $R^c$ or $R^d$ also able to form, with a radical $R^e$ or $R^f$ or $R^g$, a divalent alkene group having from 2 to 10 carbon atoms and able to have up to three olefinic double bonds;
a radical $R^{c'}$ or $R^{d'}$ also able to form, with a radical $R^{e'}$ or $R^{f'}$ or $R^{g'}$, a divalent alkene group having from 2 to 10 carbon atoms and able to have up to three olefinic double bonds.

4. The process according to claim 3, wherein in the catalytic system, the at least one ligand (A) is a ligand represented by formula (Ia'):

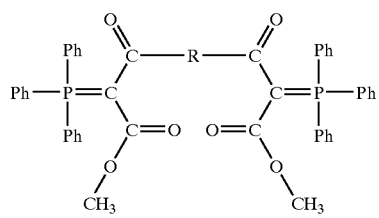

where R represents a 5,6-bicyclo[2.2.1]hept-2-ene radical.

5. The catalytic system as claimed in claim 1, wherein the nickel compound ($B_1$) is selected from:
bis(1,5-cyclooctadiene)nickel(0);
bis(cyclooctatetraene)nickel(0); and
bis(1,3,7-octatriene)nickel(0).

6. The catalytic system as claimed in claim 1, wherein, in a nickel compound (B2) or (B3), a π-allyl group has from 3 to 12 carbon atoms which do not have other aliphatic unsaturated groups, except where it contains a closed cycle.

7. The catalytic system as claimed in claim 1, wherein the nickel compound (B2) is selected from:
π-allylnickel chloride;
π-allylnickel bromide;
π-crotylnickel chloride;
π-methylallylnickel chloride;
π-ethylallylnickel chloride;
π-cyclopentylallylnickel bromide;
π-cyclooctenylnickel chloride;
π-cyclooctadienylnickel chloride;
π-cynnamylnickel bromide;
π-phenylallylnickel chloride;
π-cyclohexenylnickel bromide;
π-cyclododecenylnickel chloride;
π-cyclododecatrienylnickel chloride;
π-allylnickel acetate;
π-methylallylnickel propionate;
π-cyclooctenylnickel octoate;
π-cyclooctenylnickel methoxylate; and
π-allylnickel ethoxylate.

8. The catalytic system as claimed in claim 1, wherein the nickel compound (B3) is selected from:
bis(π-allyl)nickel;
bis(π-methallyl)nickel;
bis(π-cynnamyl)nickel;
bis(π-octadienyl)nickel;
bis(π-cyclohexenyl)nickel;
π-allyl-π-methallylnickel; and
bis(π-cyclooctatrienyl)nickel.

9. The catalytic system as claimed in claim 1, wherein the components (A) and (B) are present in amounts such that the nickel-to-ligand(s) molar ratio is between 1 and 100.

10. The catalytic system as claimed in claim 9, wherein the components (A) and (B) are present in amounts such that the nickel-to-ligand(s) molar ratio is between 2 and 50.

11. The process as claimed in claim 3, wherein:
in a first step, each of the constituents (A) and (B), which are in solution in an inert solvent, are introduced separately or simultaneously into a reactor, together with the reaction mixture; and
in a second step, the olefin or olefins are introduced, the (co)polymerization taking place at a temperature between 0 and 300° C. and at a total absolute pressure of from 1 to 200 bar.

12. The process as claimed in claim 11, wherein the constituents (A) and (B) are introduced in a nickel-to-ligand (s) molar ratio of between 1 and 100.

13. The process as claimed in claim 12, wherein the constituents (A) and (B) are introduced in a nickel-to-ligand (s) molar ratio of between 2 and 50.

14. The process as claimed in claim 11, wherein the inert solvent of constituents (A) and (B) is selected from saturated aliphatic hydrocarbons, saturated alicyclic hydrocarbons, aromatic hydrocarbons and mixtures thereof.

15. The process as claimed in claim 11, wherein the reaction mixture consists of an organic medium.

16. The process as claimed in claim 11, wherein the reaction mixture comprises a continuous liquid aqueous phase, which comprises more than 30% water by weight.

17. The process as claimed in claim 16, wherein the aqueous phase is the only liquid phase.

18. The process as claimed in claim 16, wherein the mixture comprises an organic liquid phase.

19. The process as claimed in claim 15, wherein the medium or the organic phase is selected from:
saturated aliphatic hydrocarbons, saturated alicyclic hydrocarbons, aromatic hydrocarbons and mixtures thereof; and
to the extent that the polymerization conditions keep them in liquid form, α-olefins, unconjugated dienes and mixtures thereof.

20. The process as claimed in claim 16, wherein the polymerization medium comprises a dispersing agent.

21. The process as claimed in claim 20, wherein the dispersing agent is present at up to 10% by weight for the weight of water.

22. The process as claimed in claim 21, wherein the dispersing agent is present at 0.01 to 5% by weight for the weight of water.

23. The process as claimed in claim 16, wherein the polymerization medium comprises an emulsifying agent.

24. The process as claimed in claim 23, wherein the emulsifying agent is present at up to 10% by weight, for the weight of water.

25. The process as claimed in claim 24, wherein the emulsifying agent is present at 0.01 to 5% by weight for the weight of water.

26. The process as claimed in claim 23, wherein the emulsifying agent is present in an amount greater than the critical micelle concentration.

27. The process as claimed in claim 26, wherein the amount of emulsifying agent is enough so that the polymerization takes place mainly in the micelles.

28. The process as claimed in claim 23, wherein the polymerization medium comprises a liquid organic phase and a cosurfactant.

29. The process as claimed in claim 28, wherein the cosurfactant has a solubility in water of less than $1 \times 10^{-3}$ mol per liter at 20° C.

30. The process as claimed in claim 28, wherein the cosurfactant is present at up to 10% by weight for the weight of water.

31. The process as claimed in claim 28, wherein the emulsifying agent to cosurfactant mass ratio goes from 0.5 to 2.

32. The process as claimed in claim 11, wherein the concentration of the constituent (A) in the inert solvent is between 0.1 micromol and 100 millimol per liter of solution.

33. The process as claimed in claim 11, wherein the concentration of the constituent (B) in the inert solvent is between 0.1 micromol and 200 millimol per liter of solution.

34. The process as claimed in claim 11, wherein it is carried out in an inert atmosphere.

35. The process as claimed in claim 11, wherein, in a preliminary step, the constituents (A) and (B) in solution are brought into contact with each other in their inert solvent, for a duration of 30 seconds to 10 minutes, before their introduction into the reaction mixture, this precontacting step being carried out in an inert atmosphere, at a temperature of between 0 and 100° C.

36. The process as claimed in claim 35, wherein this precontacting step is carried out at a temperature between 10 and 70° C.

37. The process as claimed in claim 11, wherein the constituents (A) and (B), which are in solution in their inert solvent, are introduced separately into the reaction mixture, the latter being held at a temperature of from 0 to 100° C.

38. The process as claimed in claim 37, wherein the reaction mixture is held at a temperature from 10 to 70° C.

39. The process as claimed in claim 11, wherein the (co)polymerization is carried out at a temperature of between 25 and 200° C.

40. The process as claimed in claim 11, wherein the (co)polymerization is carried out at a total absolute pressure of from 1 to 100 bar.

41. The process as claimed in claim 11, wherein the olefin or olefins intended to be polymerized are introduced in gas or liquid form, with enough stirring of the polymerization medium.

42. The process according to claim 11, characterized in that the olefins are chosen from ethylene, α-olefins, cyclic olefins and compounds of formula:

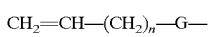

in which:

n is an integer between 2 and 20; and

G is a radical chosen from:

—OH; CHOHCH$_2$OH; OT; —CF$_3$; —COOT; —COOH; —Si(OH)$_3$; —Si(OT)$_3$;

T is a hydrocarbon radical having from 1 to 20 carbon atoms.

43. The process as claimed in claim 11, wherein at least one olefin is ethylene.

44. The process as claimed in claim 23, wherein the polymerization is carried out in the presence of an emulsifying agent, leading therefore to a latex, if necessary after a filtration step.

45. The process as claimed in claim 44, wherein the latex is a high-density polyethylene or a medium-density polyethylene or a low-density polyethylene.

46. The process as claimed in claim 24, wherein the emulsifying agent is present at up to 0.01 to 5% by weight, for the weight of water.

* * * * *

UNITED STATES PATENT AND TRADEMARK OFFICE
CERTIFICATE OF CORRECTION

PATENT NO.        : 6,818,714 B1
APPLICATION NO. : 09/936902
DATED             : November 16, 2004
INVENTOR(S)       : Atanas Tomov et al.

It is certified that error appears in the above-identified patent and that said Letters Patent is hereby corrected as shown below:

In claim 1, at col. 13, lines 16-23, please replace formula (I)' with the following:

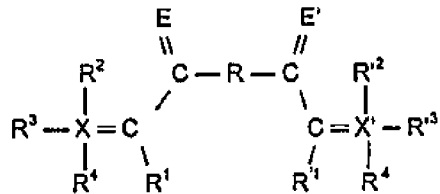

In claim 1, at col. 14, lines 2-9, please replace formula (III) with the following:

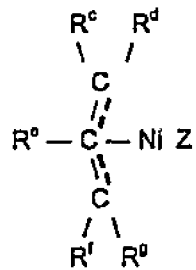

Signed and Sealed this

Second Day of October, 2007

JON W. DUDAS
*Director of the United States Patent and Trademark Office*